(12) United States Patent
Shibamoto

(10) Patent No.: US 9,096,874 B2
(45) Date of Patent: Aug. 4, 2015

(54) METHOD FOR PRODUCING LACTIC ACID UNDER PRESSURE THAT EXCEEDS NORMAL ATMOSPHERIC PRESSURE

(75) Inventor: Hiroko Shibamoto, Chiba (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 13/387,580

(22) PCT Filed: Jul. 28, 2010

(86) PCT No.: PCT/JP2010/062732
§ 371 (c)(1),
(2), (4) Date: Jan. 27, 2012

(87) PCT Pub. No.: WO2011/013721
PCT Pub. Date: Feb. 3, 2011

(65) Prior Publication Data
US 2012/0122167 A1  May 17, 2012

(30) Foreign Application Priority Data

Jul. 28, 2009 (JP) ................................ 2009-175757

(51) Int. Cl.
*C12P 7/56* (2006.01)

(52) U.S. Cl.
CPC ....................................... *C12P 7/56* (2013.01)

(58) Field of Classification Search
USPC ............................................ 435/139, 252.33
See application file for complete search history.

(56) References Cited

U.S. PATENT DOCUMENTS

| 5,234,826 A * | 8/1993 | Yamagami et al. ........... 435/139 |
| 5,541,094 A | 7/1996 | Anton et al. |
| 6,410,270 B1 | 6/2002 | Strittmatter et al. |
| 2003/0228671 A1* | 12/2003 | Hause et al. .................... 435/161 |
| 2007/0065930 A1* | 3/2007 | Wada et al. .................... 435/139 |
| 2007/0243590 A1 | 10/2007 | Takeshita et al. |
| 2010/0086980 A1* | 4/2010 | Kishimoto ...................... 435/139 |

FOREIGN PATENT DOCUMENTS

| AU | 60005/90 | * | 2/1991 |
| CA | 2022487 C | | 2/1991 |
| CN | 1856577 A | | 11/2006 |
| EP | 0 411 501 A1 | | 2/1991 |
| EP | 1 298 216 A1 | | 4/2003 |
| EP | 1669460 | * | 6/2006 |
| JP | 03-076595 | | 4/1991 |
| JP | 0 7313174 | * | 12/1995 |
| JP | 07-313174 | | 12/1995 |
| JP | 10-501984 | | 2/1998 |
| JP | 2977241 B2 | | 11/1999 |
| JP | 2000-501936 | | 2/2000 |
| JP | 2002-078495 | | 3/2002 |
| JP | 2005-528111 | | 9/2005 |
| JP | 2008-301766 | | 12/2008 |
| WO | WO-2005/033324 A1 | | 4/2005 |
| WO | WO-2006/038695 A1 | | 4/2006 |

OTHER PUBLICATIONS

International Search Report in PCT/JP2010/062732 dated Sep. 14, 2010.
Okano, K. et al. "Efficient Production of Optically Pure $_D$-lactic Acid from Raw Corn Starch by Using a Genetically Modified $_L$-Lactate Dehydrogenase Gene-Deficient and α-Amylase-Secreting *Lactobacillus plantarum* Strain", Applied and Environmental Microbiology, Jan. 2009, vol. 75, No. 2, pp. 462-467.
Zhou, S. et al. "Production of Optically Pure D-Lactic Acid in Mineral Salts Medium by Metabolically Engineered *Escherichia coli* W3110", Applied and Environmental Microbiology, Jan. 2003, vol. 69., No. 1, pp. 399-407.
First Notice of Reasons for Rejection Chinese Patent Application No. 201080032605.9 dated Jul. 15, 2013.
European Search Report dated Jun. 10, 2014 issued in Application No. 10804467.8.

* cited by examiner

*Primary Examiner* — Ralph Gitomer
(74) *Attorney, Agent, or Firm* — Foley & Lardner LLP

(57) ABSTRACT

Provided is a method for producing lactic acid, which includes: obtaining D-lactic acid or L-lactic acid by carrying out lactic acid fermentation using a lactic acid-producing microorganism under a pressurized condition that exceeds normal pressure and is capable of maintaining lactic acid production activity of the lactic acid-producing microorganism.

18 Claims, 1 Drawing Sheet

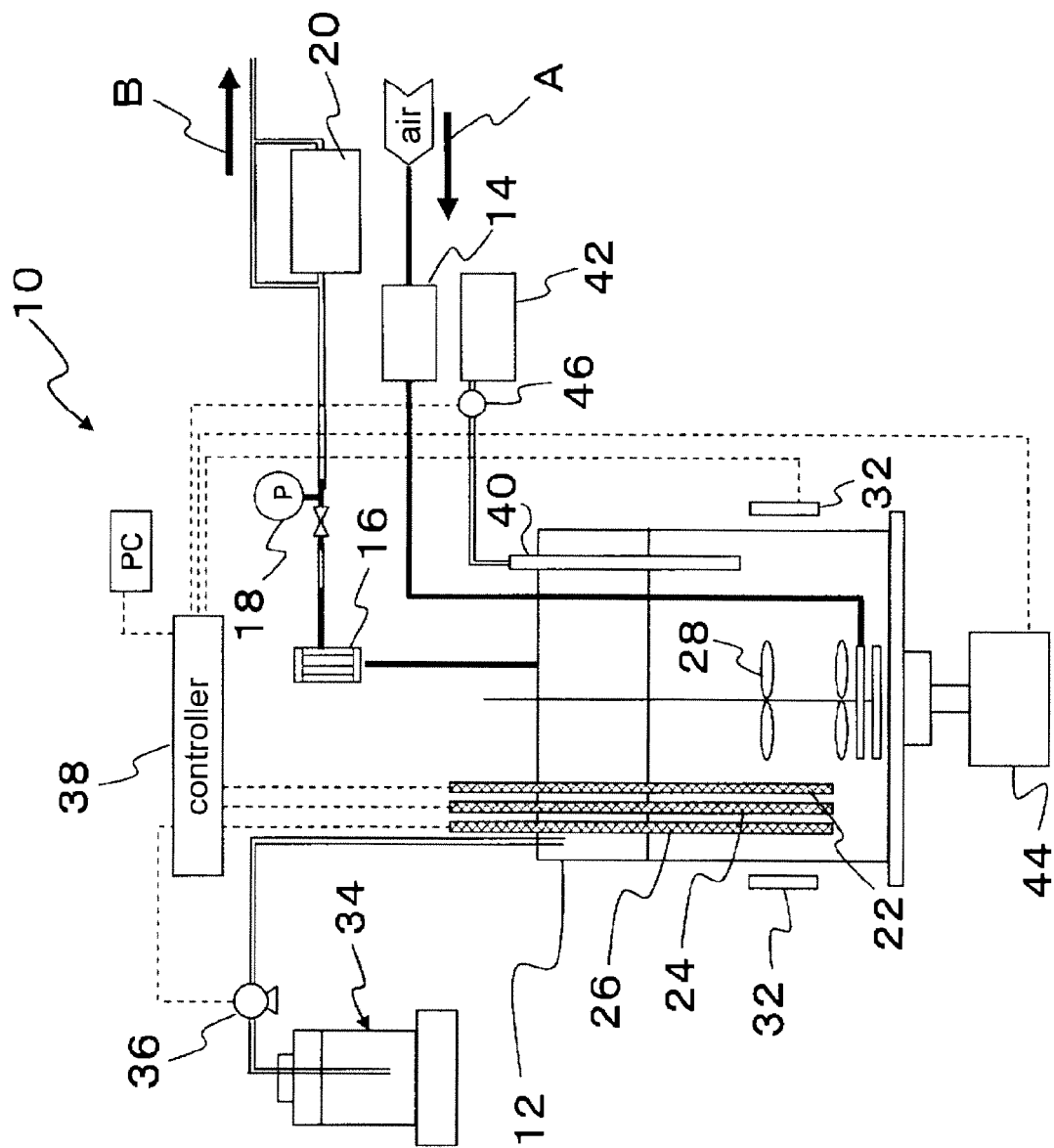

METHOD FOR PRODUCING LACTIC ACID UNDER PRESSURE THAT EXCEEDS NORMAL ATMOSPHERIC PRESSURE

This application is a National Stage application filed under 371 based upon PCT/JP2010/062732 filed Jul. 28, 2010.

TECHNICAL FIELD

The present invention relates to a method for producing lactic acid.

BACKGROUND ART

D-lactic acid has recently attracted attention as a raw material of a stereocomplex-type polylactic acid with L-lactic acid, or as a pharmaceutical intermediate. In either of the above uses, D-lactic acid as a raw material is required to have high optical purity.

Lactic acid is industrially produced by generally a fermentation method using a microorganism. A fermentation process is a process whereby a microorganism is cultured and substance production is carried out using a grown microorganism as a catalyst. Thus, the growth of a microorganism requires a source of nutrients. Corn steep liquor, which is inexpensive and often used as a source of nutrients in industry, is a nutritious liquid obtained in a process of processing corn and containing amino acids and the like at high contents. However, corn steep liquor, containing both of L-lactic acid and D-lactic acid, is one of factors that cause a reduction in optical purity.

From such a view point, for the purposes of efficient production of lactic acid and improvement in optical purity of a product, investigations have been conducted about use of raw materials not containing L-lactic acid, a reduction of the amount of L-lactic acid from raw materials or products, and the like.

For example, JP-A No. 2005-528111 employs a raw material containing no L-lactic acid and uses an oxygen uptake rate per specific microorganism as a control parameter so as to carry out adjustment such that a desired oxygen uptake rate per microorganism is maintained in a production phase. It has been reported that, as a result of the above, a high production speed of lactic acid and a high yield of lactic acid can be obtained.

JP-A No. 2008-301766 has reported that high yield of lactic acid can be obtained by employing a raw material containing no L-lactic acid and adding folic acid to a culture medium for improvement in the yield of lactic acid.

The pamphlet of WO 2005/033324 describes that L-lactic acid contained in a raw material is efficiently decomposed by using a microorganism that is modified so as to produce D-lactic acid highly selectively with high yield, thereby improving optical purity and improving the D-lactic acid productivity. It is also described that, although aeration may be completely omitted, cultivation may be performed at normal pressure, an aeration rate of from 0.1 vvm to 1 vvm, and a stirring rate of from 50 rpm to 500 rpm, that is, in the case of water at a temperature of 30° C., under aeration and stirring conditions in which an oxygen transfer rate coefficient ($k_L a$) at normal pressure is from 1/hr to 400/hr.

Such improvement in productivity by microorganism modification and raw material adjustment has an advantage in that existing equipment can be used as it is. However, it is necessary to investigate a biological activity of a lactic acid-producing microorganism, and development of a new microorganism reaction system may take time.

Meanwhile, JP-A No. 7-313174 discloses a method for processing a substrate at an applied pressure of at least 1 MPa, for example, under a condition of 100 MPa or 10 MPa, as an enzyme reaction method capable of suppressing the growth of microorganisms, such as bacteria, during reaction without reducing enzymatic activities.

JP-A No. 2002-78495 discloses an enzyme processing method capable of efficiently converting a substrate to obtain an enzyme reaction product, as an enzyme processing method capable of efficiently performing enzyme decomposition processing in a short time. It is described that this method activates an enzyme by pressure application and also improves the stability of the enzyme itself, thereby allowing for processing at a higher temperature than a normal enzyme reaction temperature. For example, enzyme processing under a condition of 150 MPa is disclosed.

SUMMARY OF INVENTION

Problem to be Solved by the Invention

An object of the present invention is to provide a lactic acid production method whereby the optical purity of lactic acid is increased in a simple and highly versatile manner.

Means for Solving the Problem

The present invention is as follows:

[1] A lactic acid production method comprising: obtaining D-lactic acid or L-lactic acid by carrying out lactic acid fermentation from sugar as a raw material using a lactic acid-producing microorganism under a pressurized condition that exceeds normal pressure and is capable of maintaining a lactic acid production activity of the lactic acid-producing microorganism.

[2] The lactic acid production method according to [1], wherein the lactic acid is D-lactic acid.

[3] The lactic acid production method according to [1] or [2], further comprising recovering the obtained lactic acid.

[4] The lactic acid production method according to any of [1] to [3], wherein the pressurized condition is adjusted with oxygen or an oxygen-containing mixed gas.

[5] The lactic acid production method according to any of [1] to [4], wherein the pressurized condition exceeds 0.10 MPa and is not more than 0.50 MPa.

[6] The lactic acid production method according to any of [1] to [5], wherein the pressurized condition is from 0.12 MPa to 0.16 MPa.

[7] The lactic acid production method according to any of [1] to [6], wherein an oxygen transfer rate (OTR) in the fermentation is in a range of from more than 0.0 mmol-$O_2$/L/hr to not more than 15.0 mmol-$O_2$/L/hr.

[8] The lactic acid production method according to any of [1] to [6], wherein an oxygen transfer rate (OTR) in the fermentation is in a range of from 1.0 mmol-$O_2$/L/hr to 15.0 mmol-$O_2$/L/hr.

[9] The lactic acid production method according to any of [1] to [8], wherein the lactic acid fermentation is carried out in a range of from pH 7.0 to pH 8.0.

[10] The lactic acid production method according to any of [1] to [9], wherein the lactic acid-producing microorganism is a lactic acid-producing *Escherichia coli*.

[11] The lactic acid production method according to any of [1] to [10], wherein the lactic acid-producing microorganism is a lactic acid-producing *Escherichia coli* having enhanced production mechanism of one of D-lactic acid or L-lactic acid as a target product, and in which a decomposition mechanism of the target product is eliminated or reduced.

[12] The lactic acid production method according to [1] to [11], wherein the lactic acid-producing microorganism is a D-lactic acid-producing *Escherichia coli* having enhanced D-lactic acid production mechanism, and in which did as the decomposition mechanism is eliminated or reduced.

According to the present invention, a lactic acid production method whereby the optical purity of lactic acid is increased in a simple and highly versatile manner can be provided.

BRIEF DESCRIPTION OF DRAWINGS

FIG. 1 is a schematic view of a fermentation apparatus used in Examples of the present invention.

EMBODIMENTS FOR CARRYING OUT INVENTION

A lactic acid production method according to the present invention is a lactic acid production method comprising: obtaining D-lactic acid or L-lactic acid by carrying out lactic acid fermentation from sugar as a raw material using a lactic acid-producing microorganism under a pressurized condition that exceeds normal pressure and is capable of maintaining lactic acid production activity of the lactic acid-producing microorganism.

In the present invention, when lactic acid fermentation from sugar as a raw material is carried out using a lactic acid-producing microorganism, the lactic acid fermentation is carried out under the pressurized condition that exceeds normal pressure and is capable of maintaining the lactic acid production activity of the lactic acid-producing microorganism. Accordingly, the optical purity of D-lactic acid or L-lactic acid, as a target, can be increased as compared to lactic fermentation carried out at normal pressure (0.10 MPa).

As a result, a versatile optical purity improvement method that is capable of increasing the optical purity of a target compound with a simple and easy operation without changing equipment extensively, and that is applicable also to a microorganism reaction system having a successful record of use, can be provided.

In the present invention, "increase the optical purity of lactic acid" means an increase in the ratio of a target optical isomer (L-lactic acid or D-lactic acid) in a recovered product. The increase in the ratio of a target optical isomer is not restricted to a case in which the production amount of one of the optical isomers as a target increases, and also includes, for example, a case in which decomposition of one of the optical isomers as a target is suppressed, a case in which decomposition of the other one of the optical isomers is promoted, and a case in which production of other by-products is suppressed.

In the present invention, the expression "under the pressurized condition that exceeds normal pressure and is capable of maintaining the lactic acid production activity of the lactic acid-producing microorganism" means a pressurized state in which a higher pressure than normal pressure is applied, and in which the pressure applied is at a level at which normal activity of the lactic acid-producing microorganism with respect to lactic acid production can be maintained.

In the present specification, the term "process" encompasses an independent process as well as any process which cannot be clearly distinguished from another process, and which attains an expected function of the process of interest.

In the present specification, the numerical range expressed using " . . . to . . . " refers to a range including respective values presented before and after "to" as a minimum valule and a maximum value, respectively.

The present invention is described below.

The lactic acid-producing microorganism usable in the present invention is not particularly restricted, and may be any microorganism that is capable of producing L-lactic acid or D-lactic acid.

In particular, microorganisms that produce or are enhanced to produce D-lactic acid are preferable, and microorganisms that have an ability to decompose an optical isomer L-lactic acid and microorganisms that act to promote the decomposition of L-lactic acid are more preferable. By using such microorganisms, the optical purity of D-lactic acid can be more efficiently increased.

The microorganism may be a microorganism, such as lactic acid bacteria, of which wild-type produces lactic acid. However, the microorganism is preferably a microorganism of which lactic acid production has been enabled or enhanced by genetic modification or the like, and, from the viewpoint of L-lactic acid decomposability, is more preferably a microorganism capable of producing lactic acid under microaerobic to aerobic conditions. Such a microorganism may be, for example, yeast, *Escherichia coli*, lactic acid bacteria, or the like, and is more preferably *Escherichia coli*, which has an abundant record of genetic modification.

As the genetically modified *Escherichia coli* as a lactic acid-producing *Escherichia coli*, any genetically modified *Escherichia coli* that has been modified to improve the production of lactic acid, for example D-lactic acid, can be used without particular limitations. Examples of such lactic acid-producing *Escherichia coli* include *Escherichia coli* in which FAD-dependent D-lactate dehydrogenase (dld) activity is inactivated or reduced, *Escherichia coli* in which expression of a gene encoding D-lactate dehydrogenase (such as ldhA) is enhanced (by, for example, introduction of a promoter of glyceraldehyde-3-phosphate dehydrogenase (GAPDH) or a promoter of serine hydroxymethyltransferase (glyA)), and heterolactic fermentation bacteria in which the activity of pyruvate formate lyase (pfl) is inactivated or reduced (APPLIED AND ENVIRONMENTAL MICROBIOLOGY, January 2003, p. 399-407). The microorganism may be a microorganism that has been subjected to a combination of these genetic modifications.

In regard to microorganisms that have been modified to improve L-lactic acid production, microorganisms in which NAD-dependent L-lactate dehydrogenase (such as Ldh2) that mainly catalyzes a reaction for synthesizing L-lactic acid from pyruvic acid is introduced or enhanced, and, microorganisms in which, independently from the above introduction or enhancement or in combination with therewith, FMN-type L-lactate dehydrogenase (such as lldD) that mainly catalyzes a reaction for decomposing L-lactic acid is deleted or reduced, can suitably be used.

The above lactic acid-producing *Escherichia coli* may be *Escherichia coli* that is modified to reduce the production of compounds other than lactic acid (by-products). Examples of such gene-modified *Escherichia coli* include *Escherichia coli* in which malate dehydrogenase (mdh) activity is inactivated or reduced and aspartate ammonia-lyase (aspA) activity is inactivated or reduced.

Such *Escherichia coli* is disclosed in, for example, JP-A No. 2005-102625 and WO 2005/033324. In particular, an *Escherichia coli* MG1655ΔpflΔdldΔmdhΔasp strain/GA-PldhA genome strain that is capable of microaerobic fermentation and described in WO 2005/033324 is preferable from the viewpoint of production efficiency of D-lactic acid. However, the scope of the invention is not limited thereto, and also includes other strains of which D-lactic acid production activity and/or L-lactic acid decomposition activity are enhanced by mutagenesis or the like.

In a case in which a microorganism of which wild-type produces lactic acid, such as lactic acid bacteria, is used as described above, genetic modification that promotes an activity to decompose the other optical isomer and/or genetic modification that reduces production of by-products may be introduced, singly or in combination, into the microorganism, without genetic modification that enables lactic acid production or genetic modification that enhances lactic acid production.

The present lactic acid production method comprises obtaining lactic acid by carrying out lactic acid fermentation from sugar as a raw material using a lactic acid-producing microorganism under a pressurized condition that exceeds normal pressure and is capable of maintaining lactic acid production activity of the lactic acid-producing microorganism (hereinafter sometimes simply referred to as "fermentation process").

The fermentation process is carried out under a pressurized condition exceeding normal pressure, namely, under a pressurized condition exceeding 0.10 MPa.

Such a pressurized condition is higher than ordinary fermentation conditions under atmospheric pressure, and it was beyond expectation that, in the production of lactic acid by a microorganism, the optical purity of lactic acid increases under such a pressurized condition.

From the viewpoint of the optical purity of the lactic acid obtained, the pressurized condition in the fermentation process is preferably more than 0.10 MPa but not more than 0.50 MPa, more preferably more than 0.10 MPa but not more than 0.20 MPa, and still more preferably from 0.12 MPa to 0.16 MPa. A pressure exceeding 0.10 MPa is preferable because the optical purity of lactic acid can be increased. On the other hand, a pressure of 0.50 MPa or less is preferable because a stress that the microorganism experiences due to the pressure is small. In addition, a pressurized condition within the above range is a so-called "micro-pressurized" condition, and thus fermentation apparatuses used in ordinary fermentation processes can be used as they are or with slight changes in equipment, such as addition of a pressurization mechanism.

The pressurized condition can be adjusted simply and easily by injection of a gas (aeration) into a fermenter.

Here, examples of the gas to be used include oxygen or an oxygen-containing mixed gas, nitrogen, and carbonic acid (carbon dioxide). The oxygen-containing mixed gas may be, for example, a mixed gas that contains 1 volume % or more of oxygen, such as air. Among them, from the viewpoints of the growth of the microorganism and the optical purity, oxygen or an oxygen-containing mixed gas is preferable. The mixed gas is preferably a mixed gas that contains from 10 volume % to 50 volume % of oxygen, from the viewpoint of the dispersibility of oxygen.

The aeration with oxygen or an oxygen-containing mixed gas may be carried out throughout the entire process of the fermentation process or only during a certain period thereof. In a case in which aeration is carried out only during a certain period of the fermentation process, aeration with oxygen or an oxygen-containing mixed gas may be carried out during a part of the growth period of the microorganism. This can be carried out simply and easily by changing the aeration condition to a gas of nitrogen, carbonic acid, or the like or to non-aeration. When aeration is carried out only during a certain period, specifically, aeration with oxygen or an oxygen-containing mixed gas is preferably carried out for one hour or longer from the start of fermentation. Here, the growth period is a period during which the microorganism grows and microorganism density in the fermenter increases.

The pH of the reaction system in the fermentation process may be an ordinary fermentation condition of from pH 6.0 to 9.0, and, from the viewpoint of the optical purity, is preferably from pH 7.0 to 8.0, and more preferably from pH 7.4 to 7.6. The pH may be adjusted using an alkali neutralizer. The kind of neutralizer that can be used is not restricted at all as long as it is neither a substance that kills microorganisms nor a substance that stops production of D-lactic acid. For example, NaOH, $NH_3$, $Ca(OH)_2$, $CaCO_3$, and the like can be exemplified.

It is not essential that a gas pass through a fermentation liquid during the aeration in the fermentation process. Depending on the shape of the fermenter, the aeration includes surface aeration in which a gas phase above the fermentation liquid is aerated while the fermentation liquid is being stirred moderately, which means that the gas is allowed to flow into the fermenter. In pressurization, it is not required that gas be filled into the fermenter and aeration be carried out. In this case, for example, the oxygen or oxygen-containing mixed gas may be filled into a hermetically sealed fermenter such that the pressurized condition is satisfied.

The aeration rate in the fermentation process may be an ordinary aeration rate of from 0 vvm to 5 vvm. An aeration rate higher than 0 vvm is preferable from the viewpoint of high optical purity, and an aeration rate of 2 vvm or less is preferable from the viewpoint of lactic acid production efficiency. An aeration rate of 1.5 vvm or less is more preferable.

In the present invention, the notation, vvm, is used for aeration rate in some cases. In the present specification, "vvm" represents the ratio of the aeration per minute relative to the liquid volume. For example, performing aeration of 10 L of fermentation liquid at 2 vvm means performing aeration at 20 L per minute.

In the case of aeration into the liquid, the rate of dissolution of oxygen into the liquid varies depending on the combination of internal pressure, the position of a stirring blade, the shape of the stirring blade, and stirring speed. Thus, various conditions can be set using the lactic acid productivity, the amounts of organic acids other than lactic acid, and the like as indices. It is unnecessary to consistently apply the set aeration conditions from the start of the fermentation to completion of the fermentation, and favorable results can be obtained even when the conditions are applied during a part of the fermentation process. Improvement in the lactic acid productivity and reduction of a non-target optical isomer can be achieved by carrying out aeration in the manner described above.

In regard to the conditions of the present fermentation process, fermentation is preferably carried out under conditions in which oxygen transfer rate (OTR) is larger than 0.0 mmol-$O_2$/L/hr but not larger than 15.0 mmol-$O_2$/L/hr (hereinafter referred to as microaerobic condition) from the viewpoint of the efficiency in the production of lactic acid with high optical purity. The OTR is preferably from 1.0 mmol-$O_2$/L/hr to 15.0 mmol-$O_2$/L/hr, more preferably from 1.0 mmol-$O_2$/L/hr to 10.0 mmol-$O_2$/L/hr, and still more preferably from 1.0 mmol-$O_2$/L/hr to 5.0 mmol-$O_2$/L/hr, from the viewpoints of the optical purity and the lactic acid productivity. The OTR mentioned above is a value measured in a lactic acid production period. Here, the lactic acid production period refers to a period in which a microorganism starts to grow and produces lactic acid after experiencing an adaptation period of microorganism cultivations after the start of fermentation. When microorganism cultivation and production of lactic acid are separately carried out, the lactic acid production period refers to a lactic acid production process.

Oxygen transfer rate (OTR) in the present invention is an oxygen transfer rate per unit volume of fermentation liquid, which can be considered also as an oxygen uptake rate of a microorganism. The OTR to be used is obtained from the following formula 1 by an exhaust gas analysis method.

$$OTR=7.22\times10^6/VL\times(QiPiyi/Ti-QoPoyo/To) \quad \text{(Formula 1)}$$

VL: Amount of liquid in the fermenter (L).
Qi and Qo: Air flow rate at an air inlet and an air outlet (L/min).
Pi and Po: Air pressure at the air inlet and outlet (MPa).
Ti and To: Absolute temperature at the air inlet and outlet (K).
yi and yo: Oxygen mole fraction at the air inlet and outlet.

In calculation of an OTR based on the above formula 1, if the difference between the air inlet and the air outlet is negligibly small with respect to the value of the air flow rate, the air pressure, or the absolute temperature, a measurement value at one place may be used. Pressure and air pressure as mentioned in the invention refer to absolute pressures.

The OTR fluctuates according to the aeration rate, stirring rotation speed, temperature, pressure, pH, and the like, because the amount of bacteria and an oxygen consumption rate per bacterial cell change during the fermentation period. Accordingly, the OTR can be adjusted to be within the range described above by appropriately adjusting the air flow rate, the air pressure, and the like.

The above OTR can be converted to another index. An example of another index is a volumetric coefficient of mass transfer ($k_L a$). The volumetric coefficient of mass transfer ($k_L a$) is a function of aeration rate and stirring rotation speed, and the following relationship is known (Formula 2, Richards, J. W. 1961, Prog. Ind. Micro. 3, 143-172).

$$k_L a \propto (P_g/V)^{0.4} V_s^{0.5} N^{0.5} \quad \text{(Formula 2)}$$

$P_g$: Power consumed by an aerated and stirred tank.
V: Amount of liquid filled into the tank.
Vs: Apparent air linear velocity (aeration rate/cross-sectional area of the tank)
N: Stirring rotation speed The correlation between OTR and $k_L a$ is expressed by the following formula 3. $k_L a$ in the fermentation process in the present invention as determined by the following relational formula is preferably larger than 0/h but smaller than 68/h, and more preferably from 4.5/h to 45/h.

$$k_L a = OTR/([DO]^* - [DO]) \quad \text{(Formula 3)}$$

[DO]*: Dissolved oxygen concentration in a fermentation liquid, which is in equilibrium with the partial pressure of oxygen in gas phase.
[DO]: Actual dissolved oxygen.

[DO]* changes in proportion to the pressure in the fermenter. Thus, in order to maintain the OTR in the fermenter constant irrespective of the pressure, it is necessary to change $k_L a$ in accordance with the pressure, specifically it is necessary to change the aeration rate and/or the stirring rotation speed. For example, pressurization causes an increase in [DO]*. Therefore, in order to maintain a constant OTR, adjustment may be made by decreasing the aeration rate or the stirring rotation speed.

According to the lactic acid production method of the present invention, in fermentation under a pressurized condition that exceeds normal pressure and is capable of maintaining lactic acid production activity of the lactic acid-producing microorganism, even when the $k_L a$ is reduced in accordance with pressurization such that the same OTR as that under a normal pressure condition is maintained, the optical purity of a target lactic acid can be increased as compared to production under the normal pressure condition.

In the present fermentation process, the pressure condition, the pH and the OTR described above may be applied in combination. In this case, the preferable ranges described for the respective conditions may be applied in appropriate combination.

In the lactic acid production method of the present invention, sugars usually used as raw materials for lactic acid production may be used as raw materials. The sugar to be used as a raw material may be any usually-used carbon source. General examples of the sugar include sugars such as starch, glucose, fructose, xylose and arabinose, or herbaceous and ligneous plants decomposition products and cellulose hydrolysates that contain such sugar components in large amounts. Furthermore, vegetable oil-derived glycerin and/or fatty acids may also be included in the raw material, together with a carbon source in the present invention.

The sugar as a raw material in the present invention may be used as a simple substance, or a vegetable-derived raw material itself can be used as raw material sugar. Preferable examples of the vegetable-derived raw material include crops such as grain, corn, rice, wheat, soybean, sugarcane, beet, cotton, and the like, or combinations thereof. The form of the raw material to be used may be a crude product, squeezed juice, ground product, or the like, and is not particularly limited. Alternatively, the raw material may be in the form including only the carbon source mentioned above.

A mixture of a plant-derived raw material and lactic acid-producing bacteria varies depending on the activity of the lactic acid-producing bacteria. In general, the concentration of plant-derived raw material in the culture medium may be set such that the initial sugar concentration in terms of glucose concentration may be 20 mass % or less with respect to the total mass of the mixture, and, from the viewpoint of sugar tolerance of the bacteria, the initial sugar concentration is preferably 15 mass % or less. Other ingredients may be added in ordinary amounts for addition to culture media for microorganisms, and the amounts thereof are not particularly restricted.

In the present invention, "fermentation" means culturing a microorganism according to the present invention using a culture medium and producing a target product. The cultivation of the microorganism and the production of the target product may be simultaneously carried out; or the microorganism may be cultured, and thereafter the target product may be produced using the microorganism obtained. Here, the culture medium to be used may be, without particular limitation, any medium that includes the carbon source, a nitrogen source, inorganic ions, and organic trace elements, nucleic acid, vitamins and the like which are required by the microorganism in order to produce lactic acid.

In particular, fermentation using a culture medium to which two or more amino acids have been added is preferable from the viewpoint of production speed. In the present invention, the culture medium to which two or more amino acids have been added means a medium that includes at least two or more among various amino acids present in nature, and also encompasses a culture medium that includes a natural product, such as yeast extract, casamino acid, peptone, whey, molasses, or corn steep liquor, or a hydrolysate of a natural product extract. In order to obtain more favorable results, a medium that includes at least one selected from yeast extract, peptone, whey, molasses, or corn steep liquor or a mixture thereof at a content of from 0.5 mass % to 20 mass % is preferable, and the content is more preferably from 2 mass % to 15 mass %. In particular, addition of corn steep liquor produces great effect. The medium or the reaction system is usually a liquid medium.

When there are plural substances corresponding to a single component in the composition, the concentration described above means the total amount of the plural substances present in the composition, unless specifically stated otherwise.

Fermentation conditions vary depending on the microorganism obtained and the fermentation apparatus. For example, the fermentation temperature is from 0° C. to 60° C., and, from the viewpoint of the growth of a microorganism, is preferably from 20° C. to 40° C., and more preferably from 25° C. to 35° C.

The fermentation time is not particularly restricted, and may be any length of time required for the bacterial cells to grow sufficiently and produce lactic acid. The fermentation time may be, for example, 15 hours or longer.

Usually, a fermenter capable of controlling temperature, pH, aeration condition, and stirring rate is generally used for fermentation. However, the fermentation in the present invention is not restricted to use of a fermenter. In the case of fermentation using a fermenter, seed bacterial cells may be cultured in advance, if necessary, as a preculture, and the precultured bacterial cells may be inoculated into a culture medium in the fermenter, which has been prepared beforehand in a required amount.

The amount of the seed bacterial cells inoculated into the culture medium is similar to that in an ordinary cultivation of a microorganism, and is not particularly restricted as long as a target product is produced. In general, the preculture solution may be inoculated in an amount of from 0.05 volume % to 15 volume % with respect to the culture medium. Further, plural kinds of lactic acid-producing bacterium may be used as the lactic acid-producing bacterium.

A fermentation product in the present invention refers to bacterial cells produced by the above-described method, fermentation liquids, and processed products thereof.

The lactic acid production method of the present invention may further include recovering the lactic acid obtained through the fermentation process (hereinafter sometimes simply referred to as "recovery process").

A commonly known method applicable to recovery of lactic acid from, for example, fermentation liquid may be used as a method for recovering lactic acid from a fermentation product, such as a fermentation liquid, obtained as described above. For example, a method of directly distilling after acidification, a method of distilling by forming lactide, a method of distilling after esterification by addition of alcohol and a catalyst, a method of extracting in an organic solvent, a method of separating by ion exchange column, a method of concentrating and separating by electrodialysis, and a method that is a combination of these methods, may be employed. The bacterial cells used in the method of the present invention have produced a group of enzymes suitable for production of lactic acid. Accordingly, further production of lactic acid using the enzymes and recovery of the lactic acid is also regarded as a part of the method for recovering lactic acid from the fermentation product.

In the lactic acid production method of the present invention, lactic acid with high optical purity can be produced. Therefore, D-lactic acid or L-lactic acid can be obtained with high purity by recovering lactic acid contained in a fermentation product obtained after the fermentation process.

In the lactic acid production method of the present invention, optical purity can be determined using a conventional HPLC or an F-Kit D-/L-lactic acid (Product No: 1112821, J. K. International).

EXAMPLES

Hereinafter, the present invention will be described in detail with reference to Examples. However, the present invention is by no means restricted thereto. Unless otherwise specified, "%" and "parts" are based on mass.

Example 1

<Preculture>

An LB medium (Difco™ LB Broth Miller) was added into an Erlenmeyer flask in a volume of 1/5 of the flask capacity, and autoclave sterilization was carried out at 121° C. for 15 minutes. Into the medium after the autoclave sterilization, 0.1 vol % of the *Escherichia coli* MG1655ΔpflΔdldΔmdhΔasp strain/GAPldhA genome strain described in WO 05/033324 was inoculated. Shaking culture was performed in a thermostatic chamber at 35° C. for 16 hours to allow the seed bacterial cells to grow.

<Fermentation>

Subsequently, 25 mL of the above preculture solution was inoculated into a 1-L fermenter (BML-01PI manufactured by ABLE Co. Ltd.) that contained 500 mL of a culture medium which had the composition shown in Table 1 and which had been subjected to autoclave sterilization. Fermentation was controlled at a pressure of 0.12 MPa, a stirring rotation speed of 260 rpm, an air aeration rate of 0.26 vvm, a fermentation temperature of 35° C., and a pH of 7.5 (adjusted with NaOH), and carried out for 48 hours.

TABLE 1

| Glucose (WAKO) | 12 wt % |
| Corn Steep Liquor (NIHON SHOKUHIN KAKO) | 3.0 wt % |
| ADEKANOL LG126 (ADEKA) | 0.03 wt % |

(adjusted to pH 7.5 with 25% (wt/vol) NaOH.)

FIG. 1 shows a fermentation apparatus 10 that was used for the fermentation.

The fermentation apparatus 10 is provided with a fermenter 12. Air is supplied from an air inlet into the fermenter 12 via a mass flow meter 14 (arrow A), whereas air inside the fermenter is discharged from an air outlet via a condenser 16 (arrow B). An intra-fermenter manometer 18 and an exhaust gas analyzer 20 are connected between the condenser 16 and the air outlet, so that the pressure inside the fermenter and the oxygen mole partial pressure at the outlet can individually be measured. A temperature sensor 22, a DO sensor 24, and a pH sensor 26 are arranged in the fermenter 12, so that the temperature, the DO (dissolved oxygen), and the pH in a reaction solution in the fermenter 12 can be measured. A disc turbine impeller 28 as a stirrer is placed in the fermenter 12. Stirring by the disc turbine impeller 28 is controlled by a magnetic stirrer 44.

A band heater 32 is provided around the fermenter 12, and a cooling bar 40 is provided inside the fermenter 12. A cool circulator 42 and a cooling-water channel-controlling electromagnetic valve 46 are connected to the cooling bar 40. A pH adjustment section 34 filled with a pH adjuster is provided outside the fermenter 12. The pH adjustment section 34 is able to supply a pH adjuster to the fermenter 12 via a pump 36.

The fermenter 12 is provided with a controller 38 that controls the entire device. The controller 38 is connected to the temperature sensor 22, the DO sensor 24, and the pH sensor 26 so that information from the individual sensors can be inputted thereinto. The controller 38 is connected to the band heater 32 and the cooling-water channel-controlling electromagnetic valve 46. In response to information from the individual sensors, the controller 38 operates the band heater 32 and the cooling-water channel-controlling electromagnetic valve 46 so as to control temperature, and also operates the pump 36 so as to control pH.

In the present Example, the value indicated by the mass flow meter 14 was employed as the air flow rate at the air inlet, and the value indicated by the mass flow meter 14 was also employed as the air flow rate at the air outlet, assuming that the reduction due to oxygen consumption is within a negligible range. Similarly, the value indicated by the intra-fermenter manometer 18 was employed as both of the air pressures at the air inlet and outlet. The value indicated by the temperature sensor 22 inside the fermenter was employed as both of the absolute temperatures at the air inlet and outlet. The oxygen mole fraction at the air inlet was assumed to be 0.21, and the value indicated by the exhaust gas analyzer 20 was employed as the oxygen mole fraction at the air outlet.

In the present Example, the air flow rate at the air inlet and outlet was set to 0.13 L/min, the air pressure at the air inlet and outlet was set to 0.12 MPa, and the temperature at the air inlet and outlet was set to 35° C. The oxygen mole fraction at the air inlet was set to 0.21, and a measured oxygen mole fraction value (from 0.21 to 0.18) was employed as the oxygen mole fraction at the air outlet. The values recorded every minute were used to obtain values calculated according to the Formula 1 above, which were then averaged to provide OTR. Here, the dissolved oxygen concentration (DO) inside the fermenter was approximately 0 ppm at or after 3 hours from the start of fermentation.

The lactic acid concentration in the resultant fermentation liquid was measured by HPLC according to an ordinary method (column: ULTRON PS-80H, eluent: perchloric acid solution (pH 2.1)). The amounts of D-lactic acid and L-lactic acid were measured by HPLC according to an ordinary method (column: SUMICHIRAL OA-5000, eluent: 2 mM copper sulfate), and substituted into the following formula to obtain the optical purity of lactic acid.

Optical purity(% ee)=(D-lactic acid concentration−L-lactic acid concentration)/(D-lactic acid concentration+L-lactic acid concentration)×100

Table 2 shows the results after the 48-hour fermentation.

Example 2

Fermentation was carried out in the same manner as in Example 1 except that the fermentation was carried out at a pressure of 0.14 MPa, whereby a target product was obtained. The results are shown in Table 2.

Example 3

Fermentation was carried out in the same manner as in Example 2 except that the fermentation was carried out at a pressure of 0.16 MPa, whereby a target product was obtained. The results are shown in Table 2.

Comparative Example 1

Fermentation was carried out in the same manner as in Example 1, but at normal pressure and an air aeration rate of 0.32 vvm, whereby a target product was obtained. The results after 48 hours are shown in Table 2.

TABLE 2

|  | Pressure (MPa) | OTR [mmol-$O_2$/L/hr] | D-Lactic Acid Accumulation Concentration [g/L] | Optical Purity [% ee] |
|---|---|---|---|---|
| Example 1 | 0.12 | 2.0 | 94 | >99.7 |
| Comparative Example 1 | 0.10 | 2.0 | 94 | 98.6 |
| Example 2 | 0.14 | 2.3 | 91.5 | >99.7 |
| Example 3 | 0.16 | 2.6 | 93.2 | 99.6 |

As shown in Table 2, the results demonstrate that D-lactic acid having high optical purity can be obtained under pressurization, compared with under normal pressure.

Example 4

Fermentation was carried out in the same manner as in Example 1, but at a pressure of 0.12 MPa, a stirring rotation speed of 200 rpm, and an air aeration rate of 0.35 vvm, whereby a target product was obtained. The results are shown in Table 3.

Example 5

Fermentation was carried out in the same manner as in Example 1, but at a pressure of 0.12 MPa, a pH of 7.4 (adjusted with NaOH), a stirring rotation speed of 200 rpm, and an air aeration rate of 0.35 vvm, whereby a target product was obtained. The results are shown in Table 3.

Example 6

Fermentation was carried out in the same manner as in Example 1, but at a pressure of 0.12 MPa, a pH of 7.6 (adjusted with NaOH), a stirring rotation speed of 200 rpm, and an air aeration rate of 0.35 vvm, whereby a target product was obtained. The results are shown in Table 3.

Example 7

Fermentation was carried out in the same manner as in Example 1, but at a pressure of 0.12 MPa, a pH of 7.0 (adjusted with NaOH), a stirring rotation speed of 200 rpm, and an air aeration rate of 0.35 vvm, whereby a target product was obtained. The results are shown in Table 3.

Example 8

Fermentation was carried out in the same manner as in Example 1, but at a pressure of 0.12 MPa, a pH of 8.0 (adjusted with NaOH), a stirring rotation speed of 200 rpm, and an air aeration rate of 0.35 vvm, whereby a target product was obtained. The results are shown in Table 3.

Comparative Example 2

Fermentation was carried out in the same manner as in Example 1, but at normal pressure, a pH of 7.0 (adjusted with NaOH), a stirring rotation speed of 200 rpm, and an air aeration rate of 0.45 vvm, whereby a target product was obtained. The results are shown in Table 3.

Comparative Example 3

Fermentation was carried out in the same manner as in Example 1, but at normal pressure, a pH of 8.0 (adjusted with NaOH), a stirring rotation speed of 200 rpm, and an air aeration rate of 0.45 vvm, whereby a target product was obtained. The results are shown in Table 3.

TABLE 3

|  | Pressure (MPa) | pH | D-Lactic Acid Accumulation Concentration [g/L] | Optical Purity [% ee] |
| --- | --- | --- | --- | --- |
| Example 4 | 0.12 | 7.5 | 93.1 | 99.2 |
| Example 5 | 0.12 | 7.4 | 92.6 | 99.3 |
| Example 6 | 0.12 | 7.6 | 94.1 | 99.2 |
| Example 7 | 0.12 | 7.0 | 85.7 | 98.7 |
| Comparative Example 2 | 0.10 | 7.0 | 84.7 | 98.3 |
| Example 8 | 0.12 | 8.0 | 95.0 | 98.6 |
| Comparative Example 3 | 0.10 | 8.0 | 94.6 | 98.0 |

From the results shown in Table 3, it is demonstrated that when the fermentation pH is adjusted to be from pH 7.0 to pH 8.0, particularly from pH 7.4 to 7.6, D-lactic acid having high optical purity can be obtained while maintaining high D-lactic acid productivity.

Example 9

250 mL of the preculture solution described in Example 1 was inoculated into a 10-L fermenter that contained 5 L of a culture medium which had the composition shown in Table 4 and which had been subjected to autoclave sterilization. Fermentation was controlled at a pressure of 0.12 MPa, a stirring rotation speed of 150 rpm, an air aeration rate of 0.24 vvm, a fermentation temperature of 35° C., and a pH of 7.5 (adjusted with NaOH), and carried out for 48 hours. The results after 48 hours are shown in Table 5.

TABLE 4

| Glucose | 12 wt % |
| --- | --- |
| Corn Steep Liquor | 3.0 wt % |
| ADEKANOL LG126 | 0.03 wt % |

(adjusted to pH 7.5 with 25% (wt/vol) NaOH.)

Example 10

Fermentation was carried out in the same manner as in Example 9, but at a stirring rotation speed of 150 rpm and an air aeration rate of 0.80 vvm, whereby a target product was obtained. The results are shown in Table 5.

Example 11

Fermentation was carried out in the same manner as in Example 9, but at a stirring rotation speed of 150 rpm and an air aeration rate of 1.50 vvm, whereby a target product was obtained. The results are shown in Table 5.

Example 12

Fermentation was carried out in the same manner as in Example 9, but at a stirring rotation speed of 100 rpm and an air aeration rate of 0.20 vvm, whereby a target product was obtained. The results are shown in Table 5.

Example 13

Fermentation was carried out in the same manner as in Example 9, but at a stirring rotation speed of 260 rpm and an air aeration rate of 1.00 vvm, whereby a target product was obtained. The results are shown in Table 5.

Comparative Example 4

Fermentation was carried out in the same manner as in Example 9, but at normal pressure, a stirring rotation speed of 100 rpm, and an air aeration rate of 0.25 vvm, whereby a target product was obtained. The results are shown in Table 5.

Comparative Example 5

Fermentation was carried out in the same manner as in Example 9, but at normal pressure, a stirring rotation speed of 260 rpm, and an air aeration rate of 1.20 vvm, whereby a target product was obtained. The results are shown in Table 5.

TABLE 5

|  | Pressure (MPa) | OTR [mmol-$O_2$/L/hr] | D-Lactic Acid Accumulation Concentration [g/L] | Optical Purity [% ee] |
| --- | --- | --- | --- | --- |
| Example 9 | 0.12 | 1.0 | 93.3 | 99.3 |
| Example 10 | 0.12 | 3.6 | 83.2 | >99.7 |
| Example 11 | 0.12 | 10.0 | 75.0 | 99.0 |
| Example 12 | 0.12 | 0.9 | 92.8 | 98.4 |
| Comparative Example 4 | 0.10 | 0.9 | 93.0 | 98.2 |
| Example 13 | 0.12 | 15.0 | 46.5 | 95.3 |
| Comparative Example 5 | 0.10 | 15.0 | 45.8 | 94.8 |

From the results shown in Table 5, it is demonstrated that D-lactic acid having high optical purity can be obtained by controlling the OTR to be within a range of from 0.9 mmol-$O_2$/L/hr to 15.0 mmol-$O_2$/L/hr, particularly within a range of from 1.0 mmol-$O_2$/L/hr to 10.0 mmol-$O_2$/L/hr.

Thus, according to the present invention, the optical purity of lactic acid can be increased in a simple and highly versatile manner.

The disclosure of Japanese Patent Application No. 2009-175757 filed on Jul. 28, 2009 is incorporated herein by reference in its entirety.

All documents, patent applications and technical standards described in the present description are incorporated herein by reference to the same extent as if each individual document, patent application, and technical standard were specifically and individually indicated to be incorporated by reference.

The invention claimed is:

1. A D-lactic acid production method comprising:
    culturing a D-lactic acid-producing *Escherichia coli* under a pressurized condition that exceeds normal atmospheric pressure and not more than 0.16 MPa to produce lactic acid from sugar as a raw material, and
    recovering the D-lactic acid produced by the D-lactic acid-producing *Escherichia coli*,
    wherein the culturing is carried out at a volumetric coefficient of mass transfer ($k_L a$) of from more than 0.0/h to not more than 45/h and an oxygen transfer rate (OTR) of from more than 0.0 mmol-$O_2$/L/hr to not more than 15.0 mmol-$O_2$/L/hr, and
    wherein the D-lactic acid has an optical purity of 99% or more.

2. The lactic acid production method according to claim 1, wherein the pressure is adjusted with oxygen or an oxygen-containing mixed gas.

3. The lactic acid production method according to claim 1, wherein the pressure is not more than 0.50 MPa.

4. The lactic acid production method according to claim 1, wherein the pressure is from 0.12 MPa to 0.16 MPa.

5. The lactic acid production method according to claim 1, wherein an oxygen transfer rate (OTR) during fermentation is in a range of from 1.0 mmol-$O_2$/L/hr to 15.0 mmol-$O_2$/L/hr.

6. The lactic acid production method according to claim 1, wherein the fermentation of lactic acid is carried out in a range of pH 7.0 to pH 8.0.

7. The lactic acid production method according to claim 1, wherein the lactic acid-producing microorganism is a lactic acid-producing *Escherichia coli* having an enhanced production mechanism of one of D-lactic acid and L-lactic acid as a target product, and in which a decomposition mechanism of the target product is eliminated or reduced.

8. The lactic acid production method according to claim 1, wherein the lactic acid-producing microorganism is a D-lactic acid-producing *Escherichia coli* having an enhanced D-lactic acid production mechanism, and in which dld as the decomposition mechanism is eliminated or reduced.

9. The lactic acid production method according to claim 1, wherein the lactic acid-producing microorganism is an organism in which FAD-dependent D-lactate dehydrogenase (dld) activity is inactivated or reduced.

10. The lactic acid production method according to claim 1, wherein the lactic acid-producing microorganism is an organism in which expression of a gene encoding D-lactate dehydrogenase is enhanced.

11. The lactic acid production method according to claim 10, wherein the D-lactate dehydrogenase is ldhA.

12. The lactic acid production method according to claim 10, wherein the gene encoding D-lactate dehydrogenase is enhanced by introduction of a promoter of glyceraldehyde-3-phosphate dehydrogenase (GAPDH) or a promoter of serine hydroxymethyltransferase (glyA).

13. The lactic acid production method according to claim 1, wherein the lactic acid-producing microorganism is an organism in which the activity of pyruvate formate lyase (pfl) is inactivated or reduced.

14. The lactic acid production method according to claim 1, wherein the lactic acid-producing microorganism is an organism in which malate dehydrogenase (mdh) activity is inactivated or reduced and aspartate ammonia-lyase (aspA) activity is inactivated or reduced.

15. The method of claim 1, wherein the OTR during fermentation is in a range of from 1.0 mmol-$O_2$/L/hr to 10.0 mmol-$O_2$/L/hr.

16. The method of claim 1, wherein the fermenting is carried out at a pH of 7.4 to 7.6.

17. The method of claim 1, wherein the OTR during fermentation is in a range of from 1.0 mmol-$O_2$/L/hr to not more than 10.0 mmol-$O_2$/L/hr, and the fermentation is carried out at a pH of from 7.4 to 7.6.

18. The method of claim 1, wherein the culturing is carried out at a temperature of 35° C.

* * * * *